(12) United States Patent
Jianzhong

(10) Patent No.: US 9,204,894 B2
(45) Date of Patent: Dec. 8, 2015

(54) ANASTOMAT FOR CIRCUMCISION

(75) Inventor: Shang Jianzhong, Anhui (CN)

(73) Assignee: Wuhu Snnda Medical Treatment Appliance Technology Co., Ltd. (CN)

( * ) Notice: Subject to any disclaimer, the term of this patent is extended or adjusted under 35 U.S.C. 154(b) by 614 days.

(21) Appl. No.: 13/000,848

(22) PCT Filed: Apr. 16, 2009

(86) PCT No.: PCT/CN2009/000406
§ 371 (c)(1),
(2), (4) Date: Aug. 16, 2011

(87) PCT Pub. No.: WO2009/155775
PCT Pub. Date: Dec. 30, 2009

(65) Prior Publication Data
US 2011/0098718 A1    Apr. 28, 2011

(30) Foreign Application Priority Data

Jun. 25, 2008 (CN) .......................... 2008 1 0115588

(51) Int. Cl.
*A61B 17/326* (2006.01)
*A61B 17/32* (2006.01)

(52) U.S. Cl.
CPC ... *A61B 17/326* (2013.01); *A61B 2017/320064* (2013.01)

(58) Field of Classification Search
CPC .... A61B 17/083; A61B 17/326; A61B 17/11; A61B 17/0644; A61B 2017/320052; A61B 2017/00876; A61B 2017/0023; A61B 2017/12095; A61B 2017/1132; A61B 2017/320064; A61B 19/24
USPC ......... 606/118, 167, 144, 157, 152, 155, 158, 606/132, 151; 30/276; 403/DIG. 9; 24/531, 24/17 B, 271, 272, 277, 279–282, 20 LS, 24/33 V–33 B, 43, 71 A, 69 SK, 70 R, 24/318–320, 578.12, 578.14, 578.13; 623/15.12, 23.72
See application file for complete search history.

(56) References Cited

U.S. PATENT DOCUMENTS

| | | | | |
|---|---|---|---|---|
| 2,857,688 | A * | 10/1958 | Haase | 36/1 |
| 3,111,124 | A * | 11/1963 | Rodbard | 606/118 |
| 3,669,115 | A | 6/1972 | Melges | |
| 4,530,525 | A * | 7/1985 | Schneider | 285/200 |
| 5,437,656 | A * | 8/1995 | Shikani et al. | 604/891.1 |
| 6,033,426 | A * | 3/2000 | Kaji | 606/213 |
| 2006/0218755 | A1* | 10/2006 | Ogino et al. | 24/20 R |

FOREIGN PATENT DOCUMENTS

| CN | 1626046 | A | 6/2005 | |
|---|---|---|---|---|
| CN | 2815285 | * | 9/2006 | ........... A61B 17/326 |

(Continued)

OTHER PUBLICATIONS

Sun, Xiaojing; International Search Report; Jul. 30, 2009; 6 pgs.; The State Intellectual Property Office, the P.R. China; Beijing, China.

(Continued)

*Primary Examiner* — Jocelin Tanner
(74) *Attorney, Agent, or Firm* — Crain, Caton & James

(57) ABSTRACT

An anastomat for circumcision related to a medical apparatus and instrument for cutting off the excess foreskin of a penis.

17 Claims, 18 Drawing Sheets

(56) References Cited

FOREIGN PATENT DOCUMENTS

| CN | 2815286 Y | 9/2006 |
|---|---|---|
| CN | 1919153 A | 2/2007 |
| CN | 101268955 A | 9/2008 |
| CN | 101313867 A | 12/2008 |
| CN | 201216624 Y | 4/2009 |
| CN | 201227313 Y | 4/2009 |
| WO | 2007145595 A1 | 12/2007 |

OTHER PUBLICATIONS

Beijer, Gijsbertus; International Preliminary Report on Patentability; Jan. 5, 2011; 8 pgs.; The International Bureau of WIPO; Geneva, Switzerland.

* cited by examiner

ANASTOMAT FOR CIRCUMCISION

CROSS-REFERENCE TO RELATED APPLICATIONS

This application claims priority from PCT/CN2009/000406 filed Apr. 16, 2009, which claims priority from Chinese Patent No. 200810115588.X filed Jun. 25, 2008, both of which are incorporated herein by reference.

STATEMENT REGARDING FEDERALLY SPONSORED RESEARCH

Not applicable.

FIELD OF THE INVENTION

The present invention relates to a medical apparatus and instrument, particularly to an apparatus and instrument for cutting off the excess foreskin of a male.

BACKGROUND OF THE INVENTION

The redundant prepuce or phimosis is one of the origins of diseases such as male urinary system disease and sexually transmitted disease, which may results in the chronic prostatitis as well as a series of symptoms such as backache, impotence and premature ejaculation. Therefore, removing the redundant prepuce or phimosis is one of the measures to prevent such diseases mentioned above.

Methods for removing the redundant prepuce or phimosis have been innovated for several times since early times of new Country, one of which is to perform a surgical operation. However, an operation inevitably produces bleeding and suffering, and the wound needs to be stitched, the patient needs to take an antiphlogistic or hang an antiphlogistic bottle as well as change dressing every day after the operation. Moreover, the stitches need to be removed after healing, which may result in walking inconvenience. Therefore, such operation is preferred to be performed under hospitalization which costs much for an entire treatment. Another method is the circumcision utilizing laser. Due to the clinical application of laser, the problem of bleeding during an operation was resolved. However, it may burn the skin and cause edema. Furthermore, the stitching of wound requires catgut and costs a longer time. The treatment required mass of antibiotics is expensive for the public. Additionally, obvious scars would occur.

There is still another method disclosed in the Chinese Patent No. 200310118525.7, titled "Tubular Anastomat For Circumcision With Bearings", in which problems such as bleeding, stitching, antiphlogistic requirements and expensive cost, which may occur during a surgical operation for removing the redundant foreskin, were resolved. However, said tubular anastomat for circumcision is arranged as an integrated sleeve equipped with an annular knife therein whose cutting edge is relatively sharp, this causes severely suffering during the operation and healing process. Moreover, since the tubular anastomat for circumcision formed into an integrated configuration whose weight cannot be ignored has to be suspended on the penis for a while after the foreskin cutting process, the patient may feel uncomfortable. Furthermore, it would directly influence the foreskin cutting as well as the postoperative recovery, if the penis becomes hyperemia due to erection. Additionally, when used, the cut deepness to the foreskin is adjusted by a spring arranged at one side of the bearing or stop collar, which is not accurate enough and hard to control.

SUMMARY OF THE INVENTION

The present invention is intended to overcome drawbacks of existing technology and provide an anastomat for circumcision, which can minimize the possibility of bleeding, suffering, suture and antiphlogistic requirements, and prevent the occurrence of penile erection during the foreskin cutting and postoperative recovery, as well as facilitate the cut deepness control, by utilizing a movable and elevating cutting knife.

In one embodiment, the present invention includes an anastomat for circumcision, comprising: i) an inner cutting ring comprising an upper casing pipe, a lower casing pipe and a connecting plate for connecting said upper casing pipe and said lower casing pipe; ii) an outer cutting ring comprising an upper sleeve, an upper circular blocking piece arranged at the upper end of said upper sleeve, a lower sleeve, and a connecting rod for connecting said upper sleeve and said lower sleeve; iii) a connecting ring comprising a casing pipe and a lower annular blocking piece arranged at the lower end of said casing pipe; iv) said upper circular blocking piece is provided with several projecting spots on its internal surface; v) said inner cutting ring is sleeved into said outer cutting ring, said upper casing pipe of the inner cutting ring has an upper end connecting to the inner side of said upper circular blocking piece of the outer cutting ring in a crimped mode, and said lower casing pipe of the inner cutting ring has a lower end connecting to the inner side of said lower annular blocking piece of the connecting ring in a crimped mode; said lower sleeve of the outer cutting ring is detachably connected with said casing pipe of the connecting ring; and vi) clearance is provided between said inner cutting ring and said outer cutting ring for accommodating the foreskin.

In another embodiment, the present invention includes an anastomat for circumcision, comprising: i) a tubular inner ring; ii) a tubular outer ring sleeved onto the outer side of said tubular inner ring; iii) an empty cavity for accommodating the foreskin arranged between said tubular inner ring and said tubular outer ring; and iv) said outer ring comprising an outer ring and another outer ring connected with each other, the end of each of the outer ring and the another outer ring being provided with a stop collar respectively, one end of said tubular inner ring being formed as a circumcision end whose external side is provided with a projecting edge, the lower end of said projecting edge being equipped with a binding strip for fastening the foreskin, the other end of said tubular inner ring being fitted with the inner side of said stop collar arranged at the end of the outer ring to axially compress against the tubular inner ring.

In yet another embodiment, the present invention includes an anastomat for circumcision, comprising: i) an outer ring for cutting and clamping; and ii) an inner ring for casing the foreskin, the external surface of said inner ring being provided with a recess, the inner side of said outer ring being provided with a knife edge, said knife edge being fitted with said recess to extrude or cut off the foreskin, said outer ring being formed into two semicircular split rings or an integrated flexible split ring having openings, each of said openings having two ends which are provided with an upper knife edge junction and a corresponding lower knife edge junction, respectively, the fringe of each of said upper knife edge junction and said lower knife edge junction being provided with a round corner, each of said upper knife edge and said lower knife edge being a single-layered knife edge or a double-layered knife edge, said double-layered knife edge being provided with a plurality of projecting spots.

In yet another embodiment, the present invention includes an anastomat for circumcision, comprising: i) an outer ring for cutting and clamping; and ii) an inner ring for casing the foreskin, the external surface of said inner ring being provided with a recess, the inner side of said outer ring being provided with knife edge, said knife edge being fitted with said recess to extrude or cut off the foreskin, saw teeth being arranged at said knife edge The anastomat for circumcision according to the present invention provides a treatment for curing redundant prepuce or phimosis without suffering, creating wounds, bleeding, stitching, taking medicine and feeling of fear. Particularly, when used, the M-type teeth included will compress the foreskin tightly, and an M-type recess of said M-type allows the analgesic provided therein, so that the whole operation may cost only several minutes. Furthermore, when finished, the patient is able to leave the treatment place immediately and the affected part will be healing in four days without leaving obvious scars, which does not influence normal working and studying.

Since its configuration of only arranging an upper casing pipe and a lower casing pipe in the upper part and lower part of the inner cutting ring and outer cutting ring respectively which are connected through a connecting plate or connecting rod, the anastomat for circumcision according to the present invention has reduced entire weight. Furthermore, the upper casing pipe of the inner cutting ring has an upper end face formed into patterns, which significantly relieves the suffering, when compared with known annular knife edge. Moreover, the connecting plate of the inner cutting ring is additionally provided with an anti-erection plate for preventing the penis from erecting, which effectively avoids the suffering due to wound produced by penile erection. Besides, the graduated ruler arranged on the external side of the connecting rod of the outer cutting ring may facilitate adjusting the crimping force produced between the outer cutting ring and connecting ring depending on the thickness of the foreskin, as well as facilitate adjusting the cut deepness of the foreskin when an elevating cutting knife is arranged between the outer cutting ring and the connecting ring. In addition, since either the upper casing pipe or the lower casing pipe of the inner cutting ring may be designed into a splicing ring, the inner diameter of the inner cutting ring may be adjusted according to the requirement of patients. Due to the moveable configuration, the elevating cutting knife may be lifted up and withdrawn back as desired, which provides a flexible operation. Finally, the present anastomat for circumcision is a disposable product which prevents the disease spreading. Therefore, the present invention provides advantages such as small and exquisite, light weight, convenient to use, as well as low cost, which is valuable to be widely popularized in general hospitals.

Additional aspects, advantages and embodiments of the invention will become apparent to those skilled in the art from the following description of the various embodiments and related drawings.

BRIEF DESCRIPTION OF THE DRAWINGS

The present invention is described below with references to the accompanying drawings in which like elements are referenced with like reference numerals, and in which:

FIG. 22-1 illustrates the configuration of the tubular inner ring formed into two semicircles in an anastomat for circumcision according to the present invention.

FIG. 22-2 illustrates the configuration of the tubular inner ring formed into a whole in an anastomat for circumcision according to the present invention.

DETAILED DESCRIPTION OF THE PREFERRED EMBODIMENTS

The following embodiments described in details with reference to the appended drawings are illustrated for the purpose of explaining the present invention only, rather than limiting the protection scope thereof.

Figure 1:
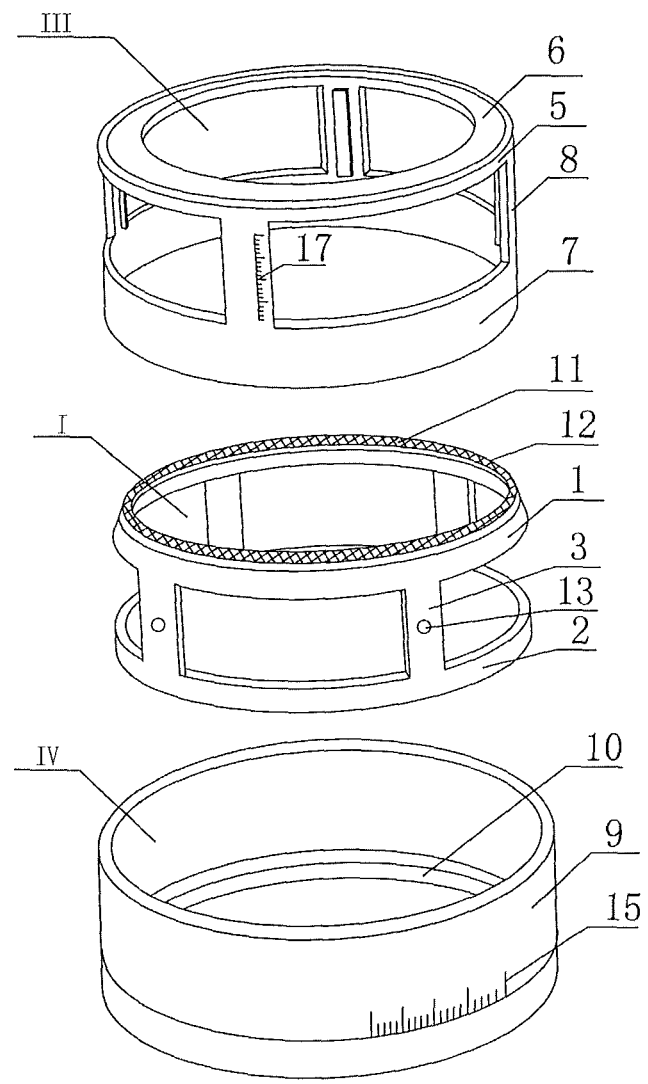
FIG. 1 illustrates an exploded assembly view of an anastomat for circumcision according to the present invention.
Figure 2:
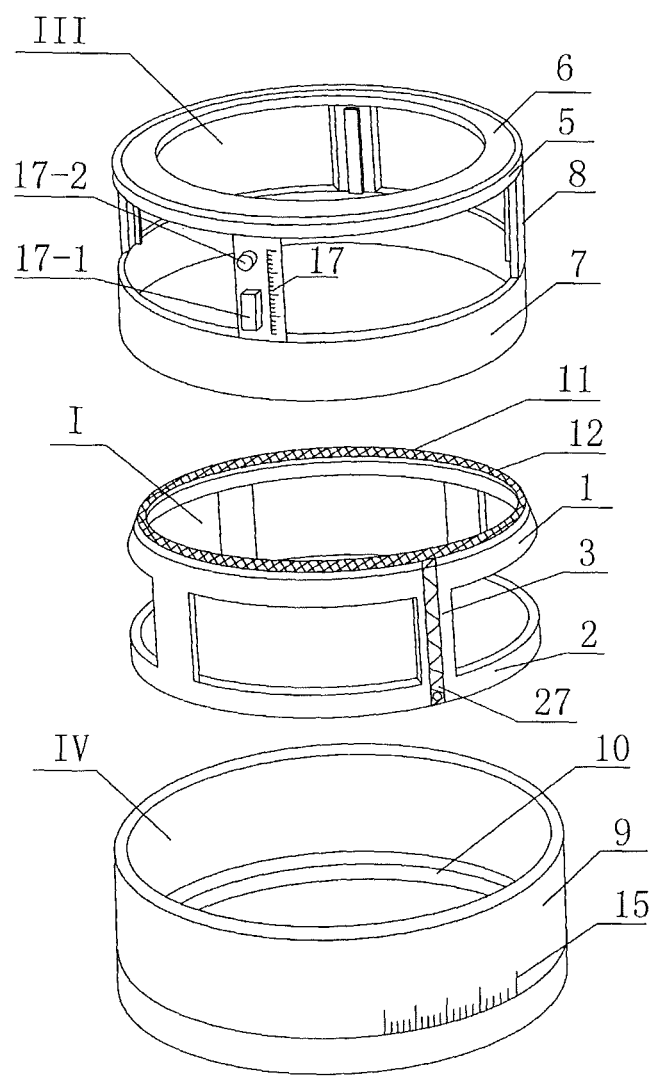
FIG. 2 illustrates another exploded assembly view of an anastomat for circumcision according to the present invention.
Figure 8:
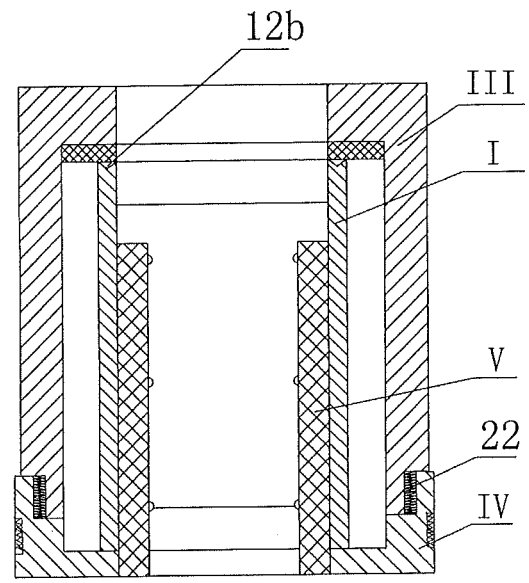
FIG. 8 illustrates a sectional view of the upper end face of a V-typed tooth formed on the section of the upper casing pipe in the inner cutting ring of an anastomat for circumcision according to the present invention.
Figure 9:
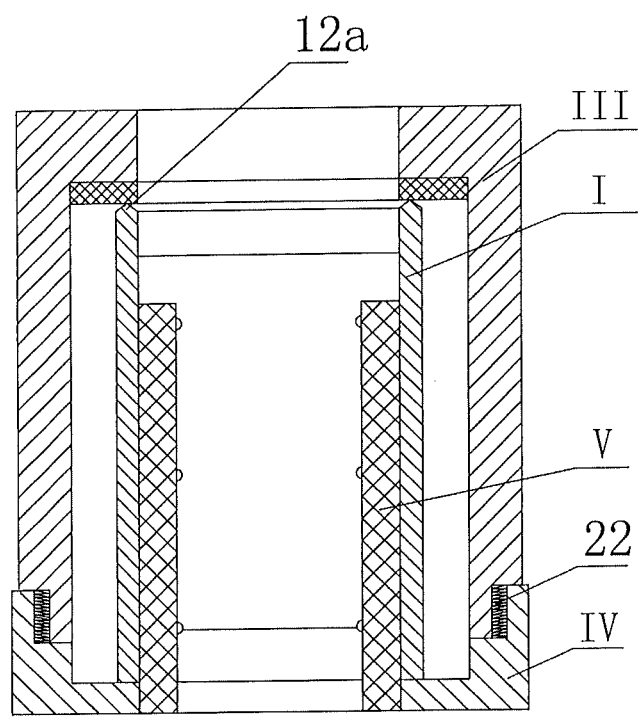
FIG. 9 illustrates a sectional view of the upper end face of an M-typed tooth formed on the section of the upper casing pipe in the inner cutting ring of an anastomat for circumcision according to the present invention.
Figure 10:
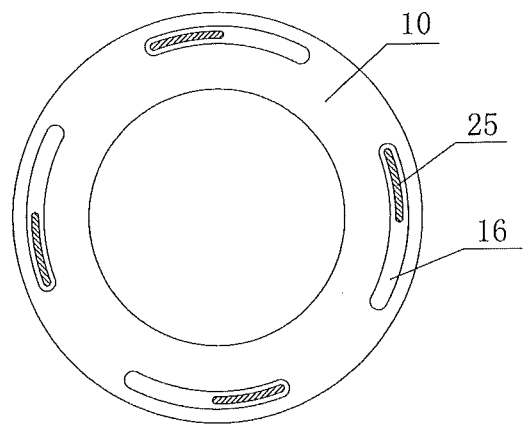
FIG. 10 illustrates a sectional view of the connecting ring in an anastomat for circumcision according to the present invention.

Refer to FIG. 1, FIG. 8 and FIG. 9, the present invention relates to an anastomat for circumcision comprising an inner cutting ring I consisted of an upper casing pipe 1 for tightly compressing the subcutaneous tissue prepuce and vessels in the foreskin to death, a lower casing pipe 2, and a connecting rod 3 for connecting said upper casing pipe 1 and lower casing pipe 2; said upper casing pipe 1 has an upper end face evenly provided with several face teeth 12 in various shapes functioning to compress against said upper casing pipe 1, each of said face teeth 12 may form into patterns 11 alternated with concave form and convex form (refer to FIG. 1), or form into a A-typed tooth 12a (refer to FIG. 9) or M-typed tooth 12b (refer to FIG. 8); said inner cutting ring I may be formed into an integrated ring or several parts spliced together; the pipe wall of said upper casing pipe 1 and lower casing pipe 2 of the inner cutting ring I may be further provided with a lacerable strip 27, through which an axial tear action may be done easily.

The anastomat for circumcision according to the present embodiment further comprises a cutting casing pipe 24 for cutting off the excess foreskin which is provided with a helix groove 14 on its pipe wall and a pipe foot 25 at its lower end; said pipe foot 25 is connected with a rotary buckle 26; said cutting casing pipe 24, pipe foot 25 and rotary buckle 26 are connected together to form an elevating tubular cutting knife II which can be lifted up and lowered down.

The anastomat for circumcision according to the present embodiment further comprises an upper sleeve 5 for fixing a blocking piece, an upper annular blocking piece 6 arranged at the upper end of said upper sleeve 5 functioning for cooperating with the upper casing pipe 1 of the inner cutting ring I so as to tightly compress the foreskin to death; a lower sleeve 7 connecting to a connecting ring; a connecting rod 8 for connecting the upper sleeve 5 with the lower sleeve 7; and an outer cutting ring III consisted of said upper sleeve 5, lower sleeve 7 and connecting rod 8.

The anastomat for circumcision according to the present embodiment further comprises a connecting ring IV consisted of an casing pipe 9 connecting with said outer cutting ring III and tightly clamping said inner cutting ring I; and a lower annular blocking piece 10 arranged at the lower end of said casing pipe 9.

Figure 6:
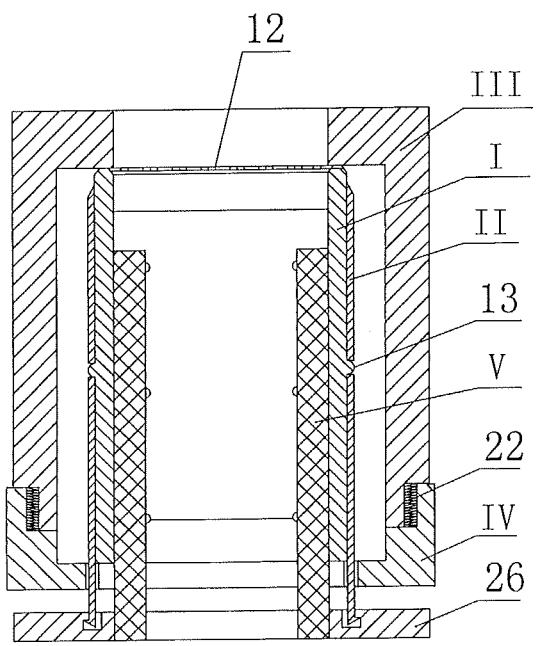
FIG. 6 illustrates a sectional view of an anastomat for circumcision without the rubber washer according to the present invention.
Figure 6A:
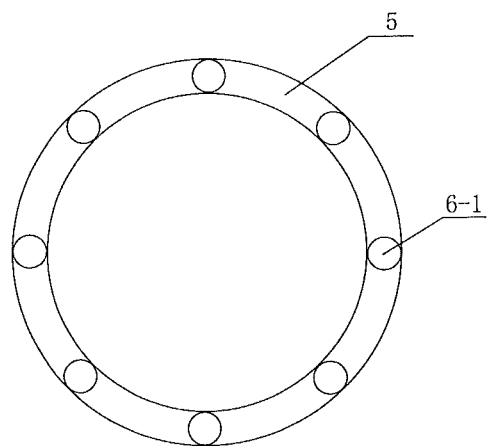
FIG. 6A illustrates a projection view of the upper annular blocking piece with projecting spots on the internal surface according to the present invention.

The anastomat for circumcision according to the present embodiment further comprises a detachable anti-erection plate V arranged at the inner side of the connecting plate 3 of the inner cutting ring I (refer to FIG. 6).

As illustrated in FIGS. 1-12, the inner cutting ring I is sleeved into the outer cutting ring III in such a manner that the upper end face of the upper casing pipe 1 of the inner cutting ring I can be connected to the inner side of the upper annular blocking piece 6 in the outer cutting ring III in a tightly crimped mode, and the lower end face of the lower casing pipe 2 of the inner cutting ring I can be connected to the inner side of the lower annular blocking piece 10 in the connecting ring IV in a tightly crimped mode; the elevating tubular cutting knife II which can be lifted up and lowered down is arranged between the inner cutting ring I and outer cutting ring III in such a manner that the pipe foot 25 at the lower end of the elevating tubular cutting knife II can pass through an arc groove 16 arranged on the lower annular blocking piece 10 of the connecting IV and then be connected to a rotary buckle 26 arranged on the elevating tubular cutting knife II; wherein, the connection between the lower casing pipe 7 of the outer cutting ring III and the casing pipe 9 of the connecting IV is a detachable connection.

Alternatively, as illustrated in FIGS. 2, 7, 8, 9, the above-mentioned embodiment may be provided without the elevating tubular cutting knife II.

The upper casing pipe 1 of the inner cutting ring I according to the present invention has an end face evenly distributed with a plurality of face teeth 12 formed into patterns 11 alternated with concave form and convex form, or formed into A-typed tooth 12a or M-typed tooth 12b; A-typed tooth 12a or M-typed tooth 12b is fitted with the inner side of the upper annular blocking piece 6 in the outer cutting ring III or a rubber washer 4 arranged in the upper annular blocking piece 6, by the way of tightly compressing against there, which functions to compress the cells, tissues and vessels at the root of the excess foreskin to death.

According to the present invention, the connecting plate 3 of the inner cutting ring I is provided with a projecting snap 13 at its external surface which can be fitted with a helix groove 14 arranged on the wall of the cutting casing pipe 24 of the elevating tubular cutting knife II, so as to enable said elevating tubular cutting knife II to be lifted up or lowered down.

When used, an anti-erection plate V provided with projecting spots is required to be inserted into the inner side of the connecting plate 3 of the inner cutting ring I during the night, so as to stimulate the external surface of the penis thus to prevent it from erection.

In order to accurately control the cutting deepness and compression deepness to the foreskin, the present invention provides a graduated ruler 17 indicating the compression deepness arranged at the outer side of the connecting rod 8 of the outer cutting ring III or arranged on the external wall of the lower casing pipe 7 of the outer cutting ring III is adoptable; moreover, a graduated ruler 15 indicating the cutting deepness to the foreskin arranged on the external wall of the casing pipe 9 of the connecting ring IV along its circumference is also feasible.

Figure 3:
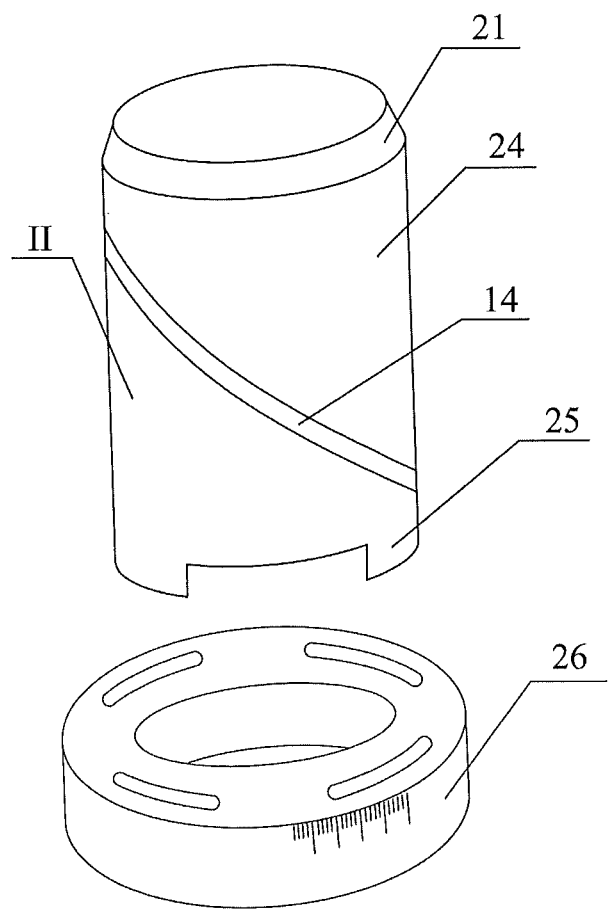
FIG. 3 illustrates a perspective view of an acute-angled cutting edge of a detachable cutting knife in an anastomat for circumcision according to the present invention.
Figure 4:
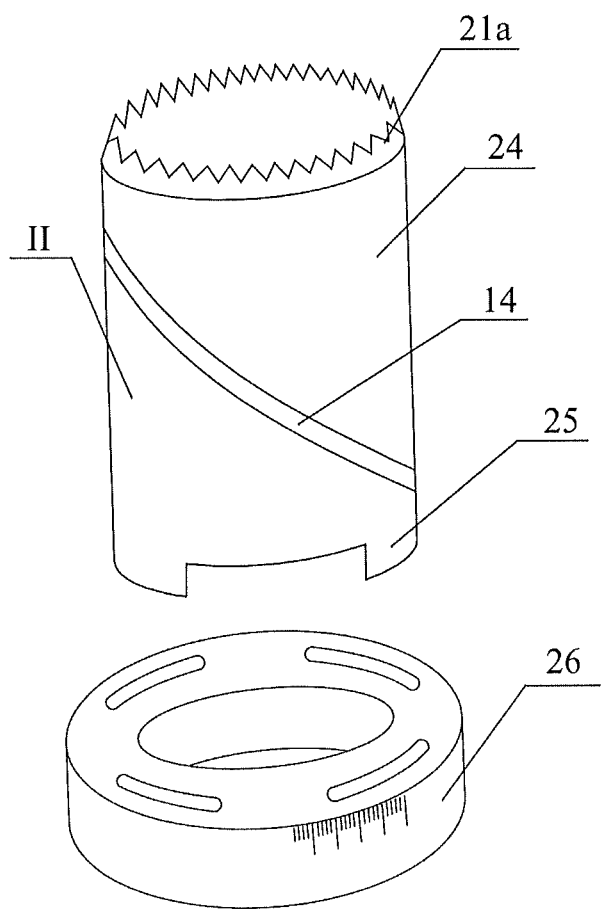
FIG. 4 illustrates a perspective view of a zigzag cutting edge of a detachable cutting knife in an anastomat for circumcision according to the present invention.
Figure 5:
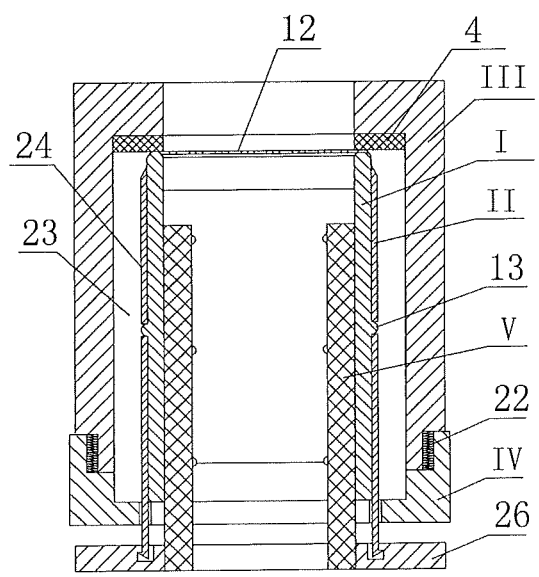
FIG. 5 illustrates a sectional view of an anastomat for circumcision provided with a rubber washer according to the present invention.

Refer to FIG. 3 and FIG. 4, according to the present invention, one end of the cutting casing pipe 24 of the elevating tubular cutting knife II may be formed into an acute-angled cutting edge 21 or zigzag cutting edge 21a. One end of said acute-angled cutting edge 21 or zigzag cutting edge 21a is allowed for compressing against the inner side of the upper annular blocking piece 6 of the crimping part so as to cut off the foreskin, or, on the contrary, not compressing against said inner side so as to return back to its original position. Alternatively, the acute-angled cutting edge 21 or zigzag cutting edge 21a is allowed for compressing against the rubber washer 4 in the upper annular blocking piece 6 so as to cut off the foreskin, or, on the contrary, not compressing against said rubber washer 4 so as to return back to its original position.

According to the present invention, the elevating tubular cutting knife II which can be lifted up and lowered down has a cutting casing pipe 24 whose inner diameter is identical with the outer diameter of the upper casing pipe 1 or lower casing pipe 2 of the inner cutting ring I.

According to the present invention, the crimping part and the connecting ring IV can be connected with each other through a thread 22.

According to the present invention, clearance 23 should be remained between each of the upper casing pipe 1, the lower casing pipe 2, the connecting plate 3 of the inner cutting ring I and each of the upper sleeve 5, lower sleeve 7 and connecting rod 8 of the outer cutting ring III, so as to accommodate the foreskin.

Figure 7:
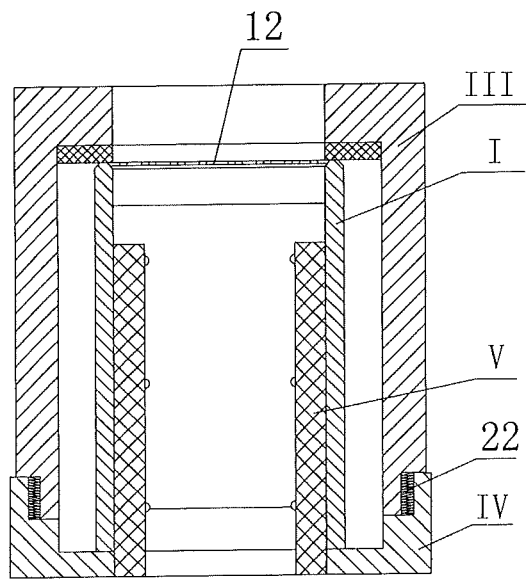
FIG. 7 illustrates a sectional view of an anastomat for circumcision provided with the rubber washer, but without the detachable tubular cutting knife according to the present invention.
Figure 11:
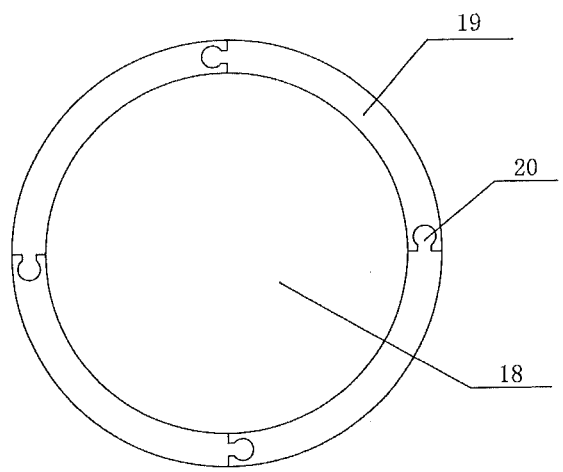
FIG. 11 illustrates the detachable casing pipes which are spliced together of the inner cutting ring in an anastomat for circumcision according to the present invention.
Figure 12:
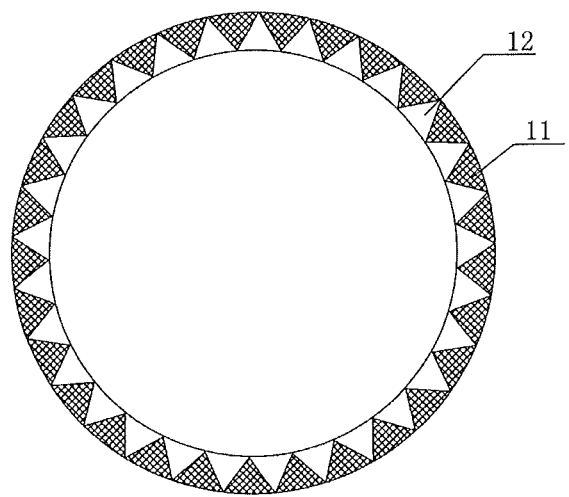
FIG. 12 illustrates a top view of the end face formed into patterns of the upper casing pipe of the inner cutting ring in an anastomat for circumcision according to the present invention.
Figure 13:
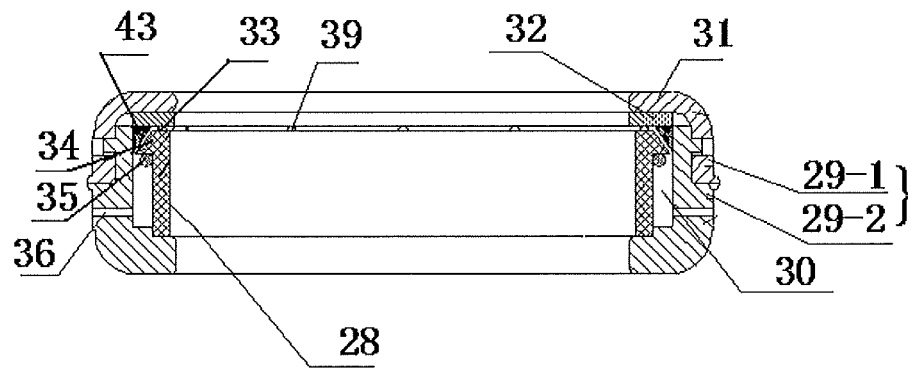
FIG. 13 illustrates a sectional view showing the assembly configuration of an anastomat for circumcision according to the present invention.
Figure 14:
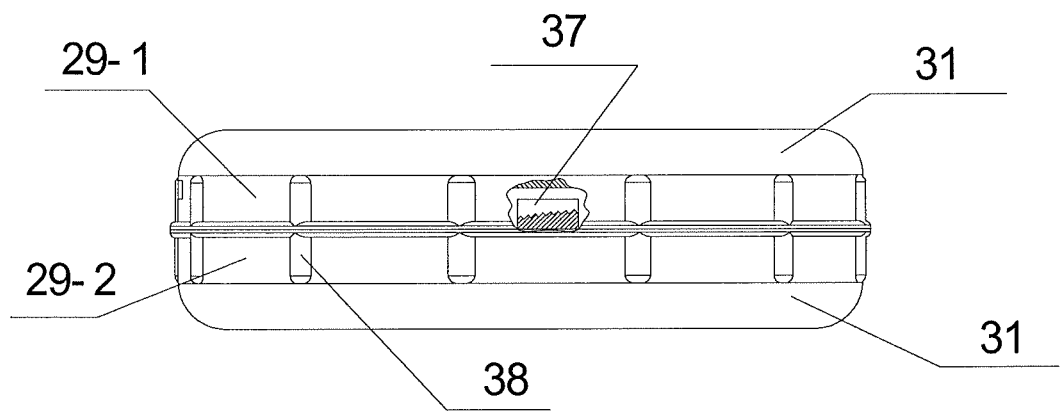
FIG. 14 illustrates the assembly configuration of an anastomat for circumcision according to the present invention.
Figure 15:
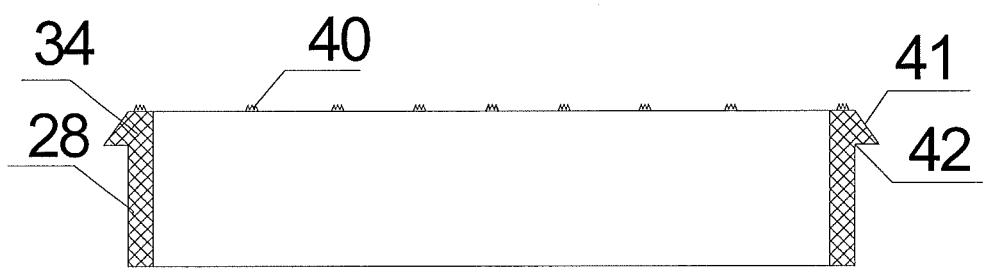
FIG. 15 illustrates a sectional view of the tubular inner ring in an anastomat for circumcision according to the present invention.
Figure 16:
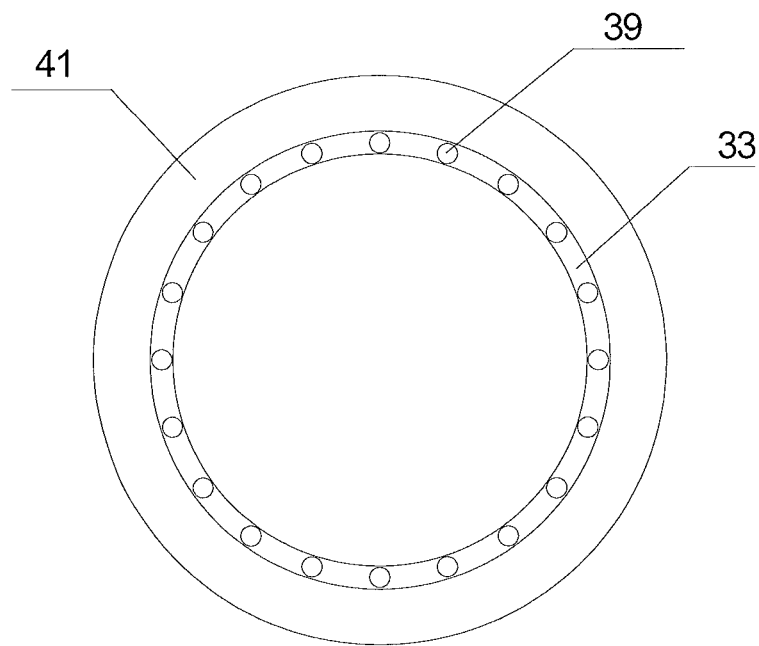
FIG. 16 illustrates a top view of the tubular inner ring in an anastomat for circumcision according to the present invention.
Figure 17:
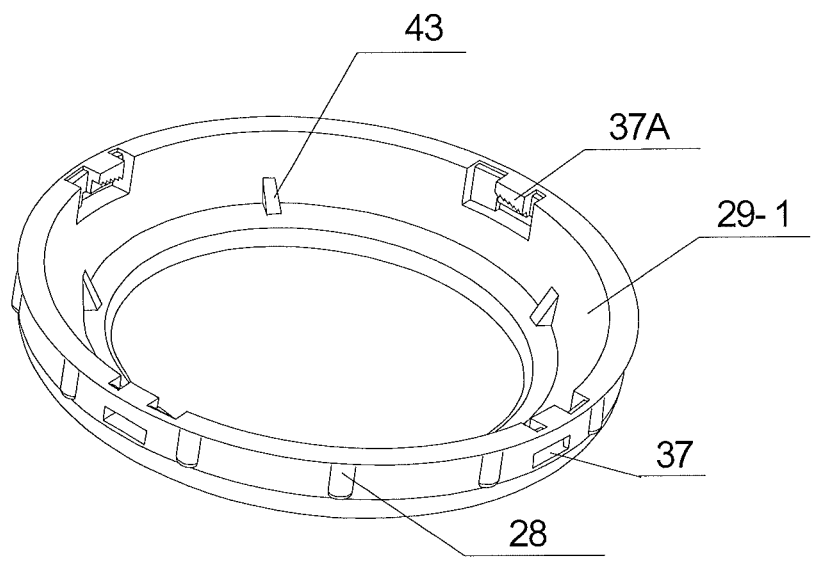
FIG. 17 illustrates the configuration of the tubular outer ring A in an anastomat for circumcision according to the present invention.
Figure 18:
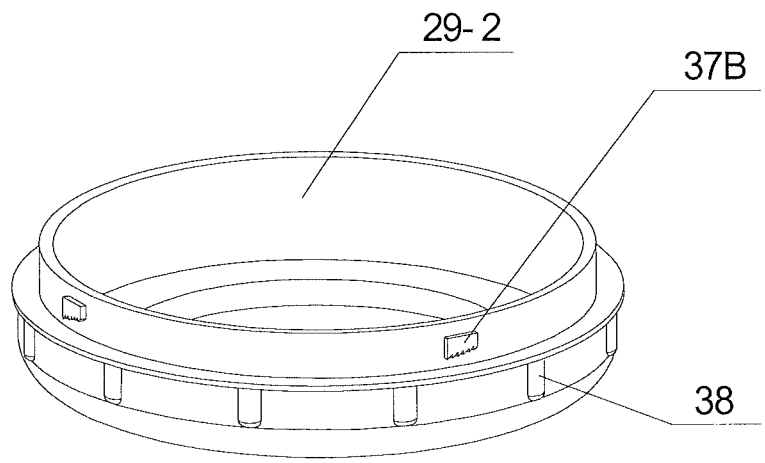
FIG. 18 illustrates the configuration of the tubular outer ring B in an anastomat for circumcision according to the present invention.
Figure 19:
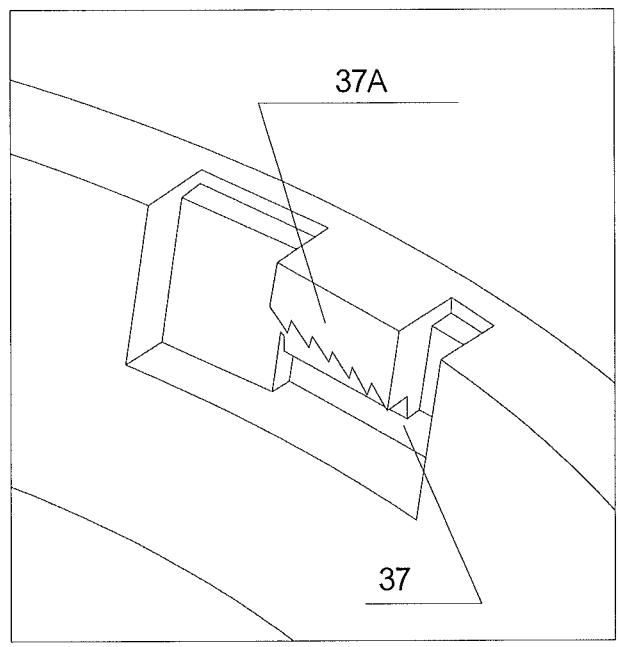
FIG. 19 is partial view of the snap-fitted configuration of the tubular outer ring A in an anastomat for circumcision according to the present invention.
Figure 20:
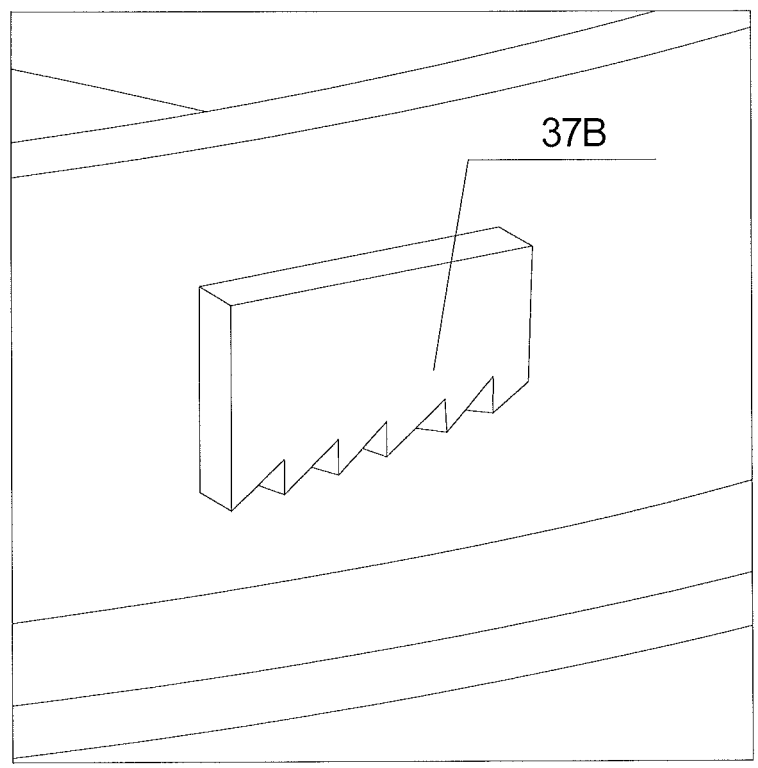
FIG. 20 is partial view of the snap-fitted configuration of the tubular outer ring B in an anastomat for circumcision according to the present invention.

As illustrated in FIG. 7 and FIG. 11, the present embodiment is distinguished from the first embodiment in that the upper casing pipe 1 and lower casing pipe 2 of the inner cutting ring I may be formed into a detachable casing pipe 18 consisted of four segments of arc plates 19 which are spliced together through snap fasteners 20. Furthermore, the pipe wall of each of said upper casing pipe 1 and lower casing pipe 2 of the inner cutting ring I is provided with a lacerable strip 27, through which an axial tear action may be done easily.

The present embodiment is distinguished from the first embodiment further in that a snap arranged on the external wall of the crimping part is clamped into a slot arranged on the connecting ring, so that the crimping part can be connected with the connecting ring in a snap-fit mode.

The present embodiment is distinguished from the first embodiment still further in that the crimping part is connected with the connecting ring IV in such a manner that a ratchet arranged on the outer cutting ring III and a thread arranged on the connecting IV is fitted with each other; wherein said ratchet is liable to be torn, so that a reuse of those cutting devices which may results in disease transmission would be prevented. Therefore, the whole assembly of those cutting devices becomes a disposable product.

When used, said inner cutting ring I, elevating tubular cutting knife II, connecting ring IV are arranged onto the outside of the penis, and the excess foreskin is turned over to be covered onto the outside of the upper casing pipe 1 of the inner cutting ring I, then the outer cutting ring III is connected with said inner cutting ring I through a thread or snap; at this time, the patterns 11 or the A-typed tooth and M-typed tooth on the face teeth 12 is gradually compressed against the inner side of the upper annular blocking piece 6 of the outer cutting ring III or to the rubber washer 4 arranged at the inner side of said upper annular blocking piece 6, so as to gradually extrude the root of the excess foreskin there between and hold back its blood circulation; finally, the rotary buckle 26 arranged at the lower end of the elevating tubular cutting knife II is rotated, which enables the helix groove 24 on the cutting casing pipe 24 to be fitted with the projecting snap arranged on the external wall of the connecting plate in the inner cutting ring I; in this way, the cutting casing pipe 24 is lifted up along said helix groove 14 so as to cut off the necrotic foreskin through the acute-angled cutting edge 21 or zigzag cutting edge 21a arranged on the end part of the cutting casing pipe 24; after that, the rotary buckle 26 is inversely rotated so as to withdraw the cutting casing pipe 24, thereby a foreskin cutting is finished.

Alternatively, the elevating tubular cutting knife II may be dismounted completely several days after the excess foreskin being compressed at its root part, when the compressed foreskin is gradually necrotic and separated from the penis automatically. Once the excess foreskin is cut off by the elevating tubular cutting knife II, or during the cutting process or healing stage, an anti-erection plate V provided with projecting spots for stimulating the penis is required to be inserted between the penis skin and the inner side of the upper casing pipe 1, lower casing pipe 2 and connecting plate 3 of the inner cutting ring I, so as to avoid penile erection which may stretch the penis. Moreover, scale marks are provide on the external side of the connecting rod 8 of the outer cutting ring III and the casing pipe 9 of the connecting ring IV, in order to control or adjust the cutting deepness to the foreskin as desired.

Another embodiment according to the present invention would be described in details below in conjunction with the appended drawings, as shown from FIGS. 13-20.

An anastomat for circumcision comprises a tubular inner ring 28, which is arranged onto the outside of the penis of a patient in such a way that the internal side of the excess foreskin is turned over and covered onto the outside of the tubular inner ring 28, then a tubular outer ring 29 is arranged onto the outside of the tubular inner ring 28; an empty cavity 30 is arranged between said inner ring 28 and outer ring 29 for accommodating the excess foreskin to be cut. Wherein, said tubular outer ring 29 is consisted of a tubular outer ring A 29-1 and a tubular outer ring B 29-2 which are connected together in a snap-fit mode. Stop collars 31 each having a washer 32 arranged at its inner side are arranged at the end parts of said tubular outer ring A 29-1 and tubular outer ring B 29-2 respectively. Said tubular inner ring 28 has one end formed into a circumcision end 33 which is provided with a projecting edge 34 at its outer side. Said projecting edge 34 is provided with a binding strip 35 at its lower end for fixing the foreskin. Once said tubular outer ring A 29-1 is snap-fitted with said tubular inner ring B 29-2 through the ratchet A 37A and ratchet B 37B, said circumcision end 33 of the tubular inner ring 28 would be fitted with said washer 32 arranged at the inner side of the stop collar 31 arranged at the end part of the tubular outer ring A 29-1 so as to extrude the foreskin. Wherein, the other end of said tubular inner ring 28 is fitted with the inner side of said stop collar 31 arranged at the end part of the tubular outer ring B 29-2 so as to axially compress against the tubular inner ring 28.

At least two through holes 36 for injecting medicine solution or cleaner fluid are arranged on the side wall of said tubular outer ring 29 or the end face of the stop collar 31; furthermore, several dismounting holes 37 for dismounting the connection between the tubular outer ring A 29-1 and tubular outer ring B 29-2 are arranged at the side wall of said tubular outer ring 29.

The external wall of said tubular outer ring 29 is provided with bumps 38 or patterns for skid resistance.

The end part of said circumcision end 33 of the tubular inner ring 28 is provided with several projecting spots 39 or saw teeth 40, through which the foreskin can be secured on the circumcision end and then be extruded.

The other end of said tubular inner ring 28 may be connected with the stop collar 31 arranged on the tubular outer ring B 29-2, so as to form into a whole to be connected with said tubular outer ring A 29-1 to extrude the foreskin.

The surface of the projecting edge of said circumcision end 33 may be designed into a taper face 41 whose lower end forms a right angle 42 with the external wall of said tubular inner ring 28; said right angle 42 provides a place where the binding strip 35 can fasten the foreskin on the external wall of the tubular inner ring 28; said taper face 41 functions to be fitted with positioning bumps 43 on a taper face or an arc face between the internal surface of the outer ring A 29-1 and the internal surface of the stop collar 31. Wherein said positioning bump 43 is arranged for the purpose of positioning the circumcision end 33 which is arranged on the tubular inner ring 28.

Said projecting edge 34 may be broken down into several segments which are evenly distributed on the circumference of the external wall of the circumcision end 33 of the tubular inner ring 28.

Said tubular inner ring 28 may be a splicing ring consisted of at least two semicircles which are spliced together.

Said outer ring may be consisted of two semicircles whose ends are connected with each other correspondingly by a clamping piece or a screw.

The anastomat for circumcision according to the present invention may be operated according to the following steps: firstly, the tubular outer ring B 29-2 and the tubular inner ring 28 are arranged onto the outside of the penis in such a way that the circumcision end 33 of the tubular inner ring 28 is faced to the glans penis, then the excess foreskin is turned over and covered onto the outside of the tubular inner ring 28. Since the projecting edge 34 arranged on the external wall of the circumcision end 33 has a lower end forming a right-angled groove 42 with the external wall of the tubular inner ring 28, the foreskin covered onto the external wall of the tubular inner ring 28 is fastened by the binding strip 35, so as to hold the excess foreskin between the tubular inner ring 28 and the tubular outer ring 29; finally, the tubular outer ring A 29-1 and tubular outer ring B 29-2 are connected with each other in a snap-fit mode. Wherein, the end parts, where the tubular outer ring A 29-1 and tubular outer ring B 29-2 are connected with each other, are provided with stop collars 31 respectively; wherein, the stop collar close to the inner side of the outer ring A 29-1 is provided with a washer 32 has a thickness, when added by the length of tubular inner ring, almost equal to the distance from the inner side of the stop collar 31 close to the tubular outer ring A 29-1 to the inner side of the stop collar 31 close to the tubular outer ring B 29-2. Therefore, when the tubular outer ring A 29-1 and the tubular outer ring B 29-2 are snap-fitted with each other, the washer 32 on the inner side of the tubular outer ring A 29-1 will be fitted with the circumcision end 33 of the tubular inner ring 28, so as to extrude the circumcision portion of the foreskin, which allows the subcutaneous tissue prepuce of the foreskin under the extruded portion necrotic due to ischemia, while the anastomat for circumcision will be separated from the penis just 5-7 days after the surgery. It can be seen from the aforesaid process that said anastomat for circumcision is convenient to operate; furthermore, it may be formed into plastic piece or stainless steel piece having small volume, light weight, simple configuration and low cost. Therefore, the present invention may be manufactured into disposable products. Additionally, since at least two through holes 36 are arranged on the side wall or the stop collar of the tubular outer ring, through which medicine solution containing analgesic, anti-inflammatory or cleaner fluid would be injected into the empty cavity, so as to relieve the patient's pain and accelerate healing.

In another embodiment according to the present invention, the anastomat may be designed into a splicing tubular inner ring 28, a splicing tubular outer ring 29 or a flexible split tubular outer ring 29, in order to adapt to various requirements from various patients. Wherein, the splicing inner ring may be formed into several pieces of inner ring which are fastened on the penis through an elastic washer, while the splicing outer ring is generally consisted of two semicircles connected with each other through two junctions, one of which is implemented by a hinge, and the other one is implemented by snap fit or fastening screw. Similarly, the ends of the opening of the flexible split tubular outer ring 29 also may be connected by snap fit or fastening screw.

Another embodiment according to the present invention would be described in details below in conjunction with the appended drawings, as shown from FIG. 21 to FIG. 31.

Figure 21:
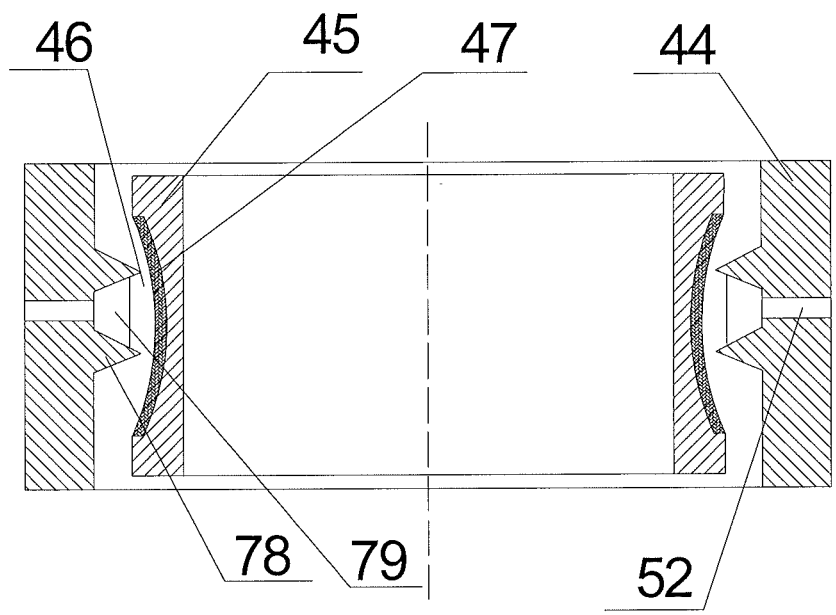
FIG. 21 illustrates the assembly configuration of an anastomat for circumcision according to the present invention.
Figures 1, 22:
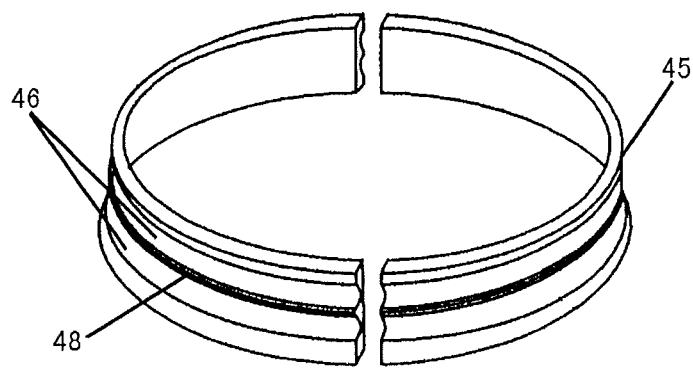
Figures 2, 22:
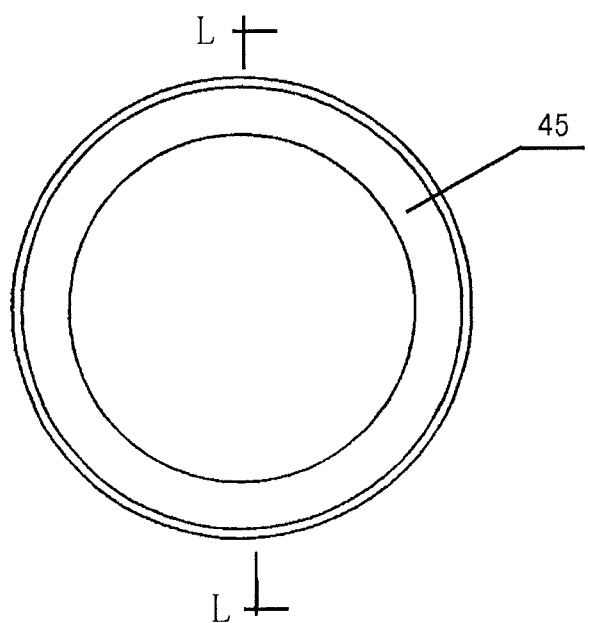
Figure 23:
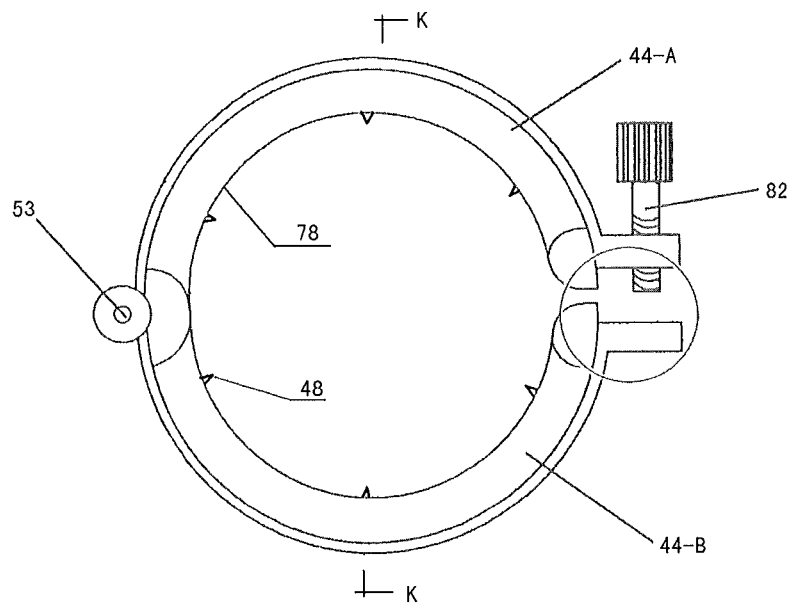
FIG. 23 illustrates the configuration of the tubular outer ring in an anastomat for circumcision according to the present invention.

As illustrated in FIGS. 21-23, an anastomat for circumcision comprises a outer ring 44 for cutting and clamping, and a inner ring 45 for covering the foreskin; said inner ring 45 may be formed into a integrated ring or two semicircles or more than two arc segments; said inner ring 45 is provided with at least one circle of recess 46 on its external surface; said recess 46 is provided with an elastic washer 47 on its surface; said outer ring 44 is provided with at least one circle of knife edge 78 whose fringe is evenly distributed with several saw teeth or projecting spots 48; said knife edge 78 is fitted with said recess 46 so as to extrude and/or cut the foreskin; channels 52 for injecting medicine solution, which are communicated with the empty cavity between said outer ring 44 and inner ring 45, are arranged on the side wall of said outer ring 44.

The inner ring 45 and outer ring 44 included in the anastomat for circumcision may be made of high-grade 372-type organic material without toxic and side-effect.

The outer ring 44 may be consisted of a left semicircle part 44-A and a right semicircle part 44-B; alternatively, the outer ring 44 may also be an integrated flexible split ring. Each of the semicircle part and the flexible split ring has two junctions, one of which can be implemented by a connecting snap 53, while the other one can be implemented by a fastener 75 and an unlocking hole 76; of course, the outer ring 44 may also be formed as an integrated configuration having an opening which can be connected with the fastener 75. The fastener 75, which would be explained below through examples, may be implemented in the form of fastening screw 82 or other connection.

Figure 24:
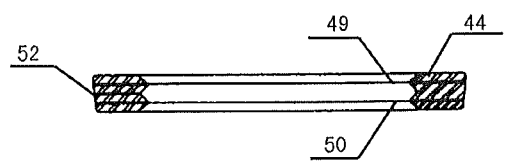
FIG. 24 illustrates a sectional view of the tubular outer ring in an anastomat for circumcision along K-K line according to the present invention.
Figure 25:
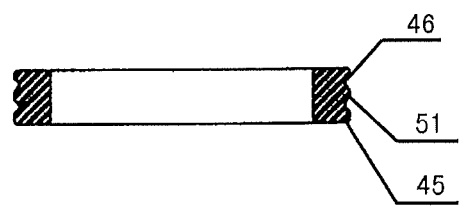
FIG. 25 illustrates a sectional view of the tubular inner ring in an anastomat for circumcision along L-L line according to the present invention.

FIG. 24 illustrates the K-K directional cross-sectional view of the outer ring of an anastomat for circumcision according to one embodiment of the present invention;

FIG. 25 illustrates the L-L directional cross-sectional view of the inner ring of an anastomat for circumcision according to one embodiment of the present invention. As illustrated, the present invention focuses on following technical features: said two semicircular split rings or said integrated flexible split outer ring 44 are/is provided with two circles of snap rings 49, 50 thereon, while said inner ring 45 is provided with recesses 46 thereon which are fitted with said snap rings 49, 50; said recesses 46 are provided with convex 51 there between; said inner ring 45 is consisted of a left ferrule and a right ferrule configured to be spaced apart from each other with a junction, and there is a round corner arranged at said junction. The inner ring 45 and outer ring 44 are fitted with each other, so as to clamp the foreskin to be cut off. In this way, the foreskin will be necrosis due to a blood circulation failure. Due to the unavoidable occurrence of infection during the operation, the assistant treatment of medicine solution is required to eliminate inflammation and facilitate skin renewal, which allows for further accelerating healing. The medicine solution accommodated within the empty cavity mentioned-above directly penetrates into the infection portion so as to eliminate inflammation and facilitate skin renewal. Such medicine solution specifically prepared for a circumcision whose prescription has no reference to the present invention will not be given unnecessary details here.

Since known operation for fastening the connecting part A of the outer ring 44 is extremely inconvenient which causes patients to be went under the knife extremely suffering, this reinforce their sense of fear and increase the duration of surgery. Several types of connection configuration would be provided below.

Figure 26A:
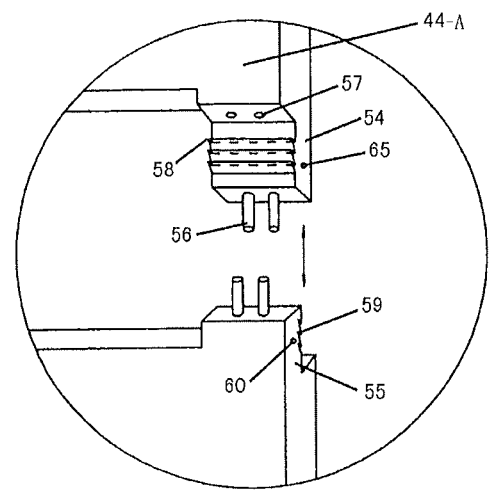
FIG. 26A illustrates the enlarged details of a configuration of part A of the tubular outer ring in an anastomat for circumcision according to the present invention.

FIG. 26A illustrates enlarged detail of a configuration of part A of the outer ring 44 in an anastomat for circumcision according to one embodiment of the present invention. Said outer ring 44 is consisted of two semicircle parts 44-A, 44-B, and a connecting snap 53 for connecting one end of said semicircle part 44-A and one end of said semicircle part 44-B, while the other ends of the semicircle parts are provided with L-shaped parts 54, 55 respectively, which are fitted with each other. A connecting rod 56 and a connecting hole 57 are arranged on the top end and bottom platform of each of said L-shaped parts 54, 55, respectively. Wherein, the connecting rod 56 arranged on one end of a semicircle part is fitted with the connecting hole 57 arranged on the other end of the remaining semicircle part. Each of said L-shaped parts has a vertical end whose internal side is provided with a dentoid protuberance 58 or dentoid groove 59, wherein the dentoid protuberance 58 or dentoid grooves 59 on one L-shaped part is fitted with the dentoid groove 59 or dentoid protuberance 58 on the internal side of the vertical end of the remaining L-shaped part. In such a manner, nothing but to simply insert the connecting rod 56 into the connecting hole 57 and hold it therein, meanwhile make the dentoid protuberance 58 and the dentoid grooves 59 fitting with each other, so as to close the whole outer ring 44 in a locking way, when it's desired to lock the semicircle parts 44-A, 44-B together. The operation of inserting a screwdriver or other tool into a hole 44 arranged on the L-shaped part so as to destroy the whole configuration therein by acting a slight force thus to open the anastomat for circumcision in the present embodiment is also possible, when it's desired to break the closed configuration (since the present embodiment is a disposal anastomat for circumcision).

Figure 26B:
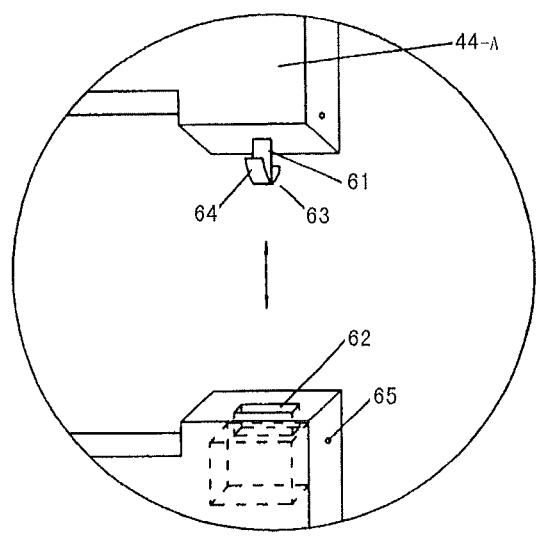
FIG. 26B illustrates the enlarged details of another configuration of part A of the tubular outer ring in an anastomat for circumcision according to the present invention.

FIG. 26B illustrates the enlarged detail showing another configuration of part A of the outer ring 44 in an anastomat for circumcision according to one embodiment of the present invention. Said outer ring 44 is consisted of two semicircle parts 44A, 44B and a connecting snap 53 for connecting one end of said semicircle part 44-A and one end of said semicircle part 44-B, while the other ends of the semicircle parts are provided with a hook-like protuberance 61 or slotted hole 62 respectively, the hook-like protuberance 61 or slotted hole 62 arranged at said semicircle part 44-A is fitted with the slotted hole 62 or hook-like protuberance 61 arranged at said semicircle part 44-B. Said hook-like protuberance 61 includes a connecting plate 63 and an inverted-V type clamping piece 64; said connecting plate 63 has one end connecting to the end part of the semicircle part 44-A and the other end connecting to the middle part of the clamping piece 64; said inverted-V type clamping piece 64 is configured to possess both considerable flexibility and certain hardness, such as stalloy, while said slotted hole 62 has an opening with relatively larger caliber and the internal empty cavity 50 has a relatively larger volume. Said semicircle part 44-A is provided with a hole 65 at the end thereof, which plays the same role as that of the hole 60 shown in FIG. 26A. When it's desired to lock the outer ring 44, the hook-like protuberance 61 is inserted into the slotted hole 62, at this time, the clamping piece 64 is fixed and positioned due to its elastic characteristic and then resist against the internal wall of the slotted hole 62 due to its hardness characteristic, so as to be locked there.

Figure 26C:
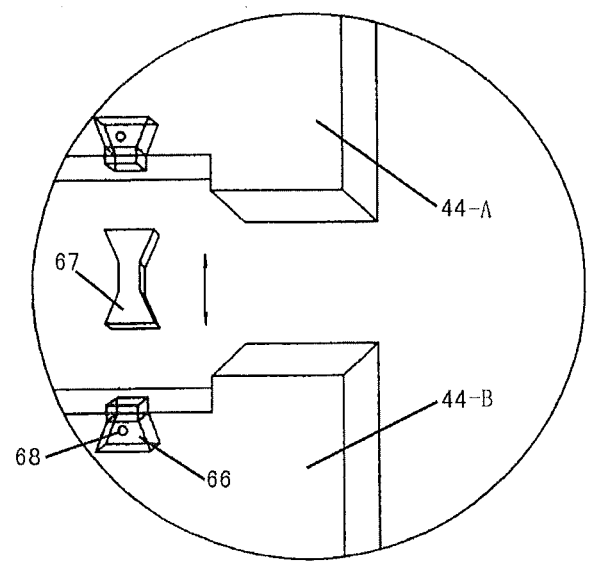
FIG. 26C illustrates the enlarged details of still another configuration of part A of the tubular outer ring A in an anastomat for circumcision according to the present invention.

FIG. 26C illustrates the enlarged detail showing still another configuration of part A of the outer ring 44 in an anastomat for circumcision according to one embodiment of the present invention. Said outer ring 44 is consisted of two semicircle parts 44-A, 44-B and a connecting snap 53 for connecting one end of said semicircle part 44-A and one end of said semicircle part 44-B, while the other ends of the semicircle parts are provided with concave slotted holes 66 respectively. Each of said concave slotted holes 66 receives a bow tie-like block 67. Said semicircle part 44-A is provide with a hole 68 on its end part which plays the same role as those of the holes 60, 62 mentioned above. When it's desired to lock the outer ring 44, both ends of the bow tie-like block 67 are inserted into the concave slotted holes 66 respectively.

Figure 26D:
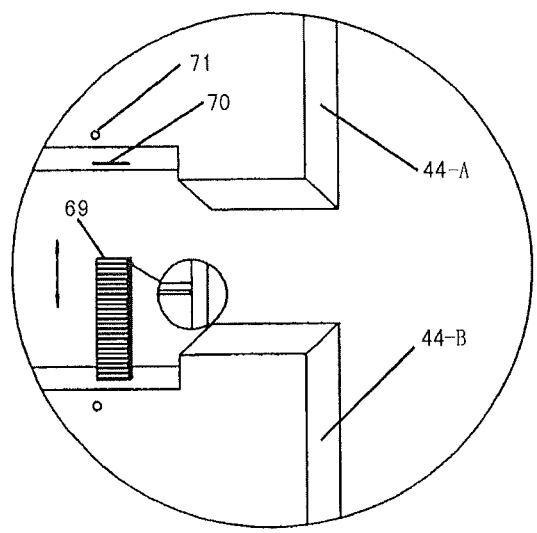
FIG. 26D illustrates the enlarged details of further another configuration of part A of the tubular outer ring in an anastomat for circumcision according to the present invention.

FIG. 26D illustrates the enlarged detail showing still another configuration of part A of the outer ring 44 in an anastomat for circumcision according to one embodiment of the present invention. Said outer ring 44 is consisted of two semicircle parts 44-A, 44-B and a connecting snap 53 for connecting one end of said semicircle part 44-A and one end of said semicircle part 44-B, while the other ends of the semicircle parts are provided with bar-type denticles 69 or bar-type sprocket holes 70 respectively. It can be seen from the enlarged details of the bar-type denticle 69 that there are a plurality of small horizontal-strip style protuberances laterally arranged thereon which are fitted with several small recesses laterally arranged in the bar-type sprocket hole 70, so as to be clamped and further locked therein, when the bar-type denticle 69 is inserted into the bar-type sprocket hole 70. It should be noticed that the function of clamping and locking is unidirectional, which requires tilt direction of both said small horizontal-strip style protuberances of the bar-type denticle 69 and that of the small recesses in the bar-type sprocket hole 70 form an obtuse angle with insertion direction. That is to say, once locked and positioned, the bar-type denticle 69 won't be simply pulled out from the bar-type sprocket hole 70 under normal circumstances, which ensures a firm locking and provides a good operability. The present embodiment also provides holes for destroying the connection of the outer ring as mentioned above. When it's desired to open the closed configuration, a screwdriver or other tool may be inserted into the hole 71 so as to destroy the whole configuration therein by acting a slight force thus to open the anastomat for circumcision in the present embodiment.

Figure 31:
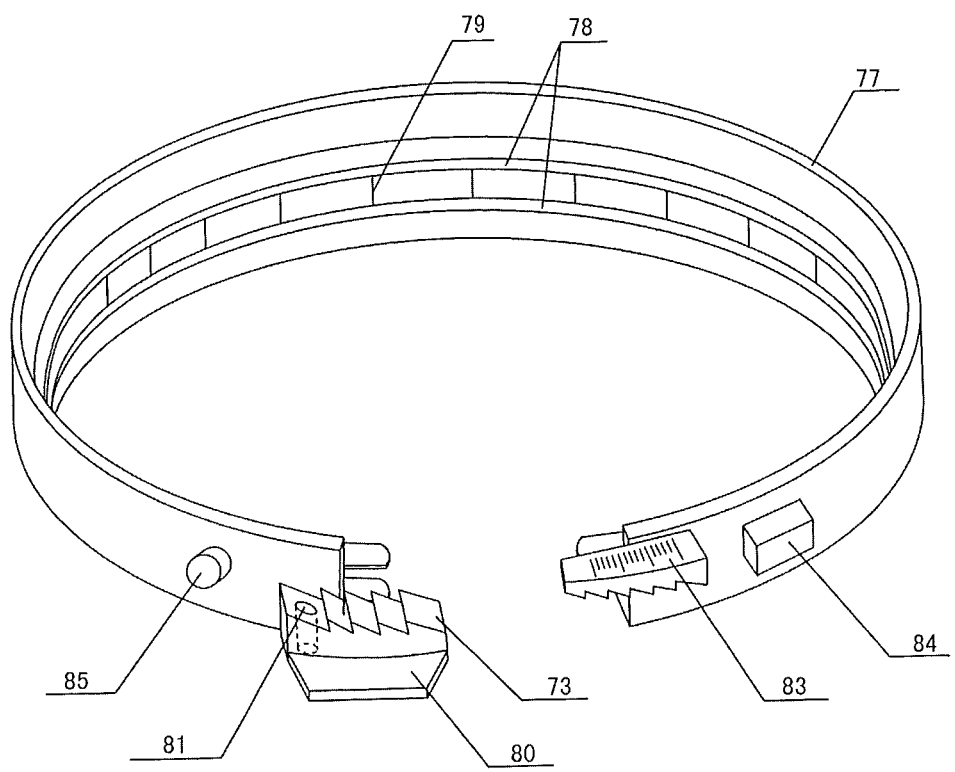
FIG. 31 illustrates the configuration of the tubular outer ring formed into an integrated flexible split ring in an anastomat for circumcision according to the present invention.

FIG. 31 illustrates an outer ring formed into an integrated flexible split ring 77 according to the present invention. The opening of said split ring 77 provides two ends equipped with knife edge junctions respectively which are corresponding to each other; said knife edge may be formed into a double-layered knife edge sandwiched with several cutting pieces 79 vertically therebetween. Each of said knife edge junctions is provided with a first ladder snap-fitted block 73, a second ladder snap-fitted block 74, an unlocking stem 80, an unlocking hole 81, a graduated ruler 83, a digital ruler 84 and an alarm 85.

FIGS. 27-30 illustrate the outer ring of an anastomat for circumcision according to another embodiment of the present invention. Said outer ring 44 has an opening of which the ends are provided with an upper knife edge 72A junction and a lower knife edge 72B junction correspondingly, respectively. One end of said opening, where the upper knife edge 72A junction is arranged, is provided with a first ladder snap-fitted block 73, the other end of said opening, where the lower knife edge 72B junction is arranged, is provided with a second ladder snap-fitted block 74, and the first ladder snap-fitted block 73 and the second ladder snap-fitted block 74 are fitted with each other. In the section, the first ladder snap-fitted block 73 is positioned below the upper knife edge 72A junction, while the second ladder snap-fitted block 74 is positioned above the lower knife edge 72B junction. When used, the lower knife edge 72B junction is inserted into a position under the upper knife edge 72A junction, while the second ladder snap-fitted block 74 is clamped above the first ladder snap-fitted block 73, so that the first and second ladder snap-fitted blocks 73, 74 can be tightly engaged with each other due to the position limiting function of the upper and lower knife edge 72A, 72B junctions. In such a way, the whole outer ring can be locked strictly. The first ladder snap-fitted block 73 or the second ladder snap-fitted block 74 is provided with a hole 65, so that a screwdriver or other tool may be inserted therein and destroy the whole configuration by acting a slight force thus to open the anastomat for circumcision in present invention (since the anastomat for circumcision in present invention is a disposal one).

Under given several designs of the connection configuration, the operation of the anastomat for circumcision according to the present invention would be provided as follows:

Step 1, cleaning and disinfecting the penis, and push the foreskin which covers the glans backwards, so that it can be exposed completely;

Step 2, adjusting and positioning the inner ring, then pulling out the foreskin which has been pushed backwards, until it completely covers the inner ring and the glans;

Step 3, opening the outer ring, then arranging it onto the outside of the inner ring and fixing it thereon, so that the foreskin will be necrosis due to a blood circulation failure;

Step 4, injecting medicine solution into the empty cavity through the channel, by which the medicine solution would be directly supplied to the affected part, so as to diminish inflammation and relieve pains;

Step 5, removing the necrotic foreskin after 2-5 (or a little more) days, meanwhile loosening the outer ring or later.

A foam-rubber mattress arranged between the outer ring and inner ring may reduce the stress produced during the foreskin cutting process.

Known anastomat for circumcision usually comprises an inner ring formed into an integrated circle whose diameter remains unchanged may aggravate the uncomfortable feeling. What is illustrated is an exploded view showing the anastomat for circumcision according to another embodiment of the present invention. Wherein, known integrated inner ring is improved into a left semicircle part 45-1 and a right semicircle part 45-2, so as to adapt to the circumstance that the penis may be erected and enlarged. In this way, the extrusion force may be reduced.

Figure 27:
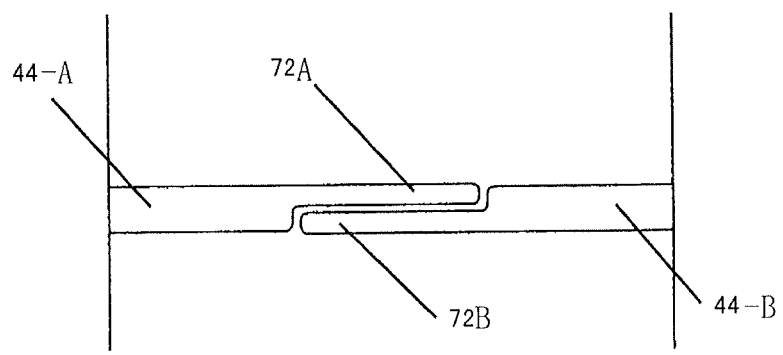
FIG. 27 illustrates the sectional configuration of the upper and lower single-layered knife edge junctions of an anastomat for circumcision along M-M line according to another example in the present invention.
Figure 28:
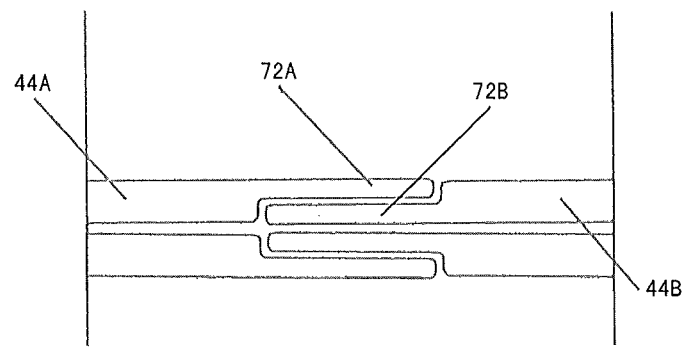
FIG. 28 illustrates the sectional configuration of the upper and lower double-layered knife edge junctions of an anastomat for circumcision along M-M line according to another example in the present invention.
Figure 29:
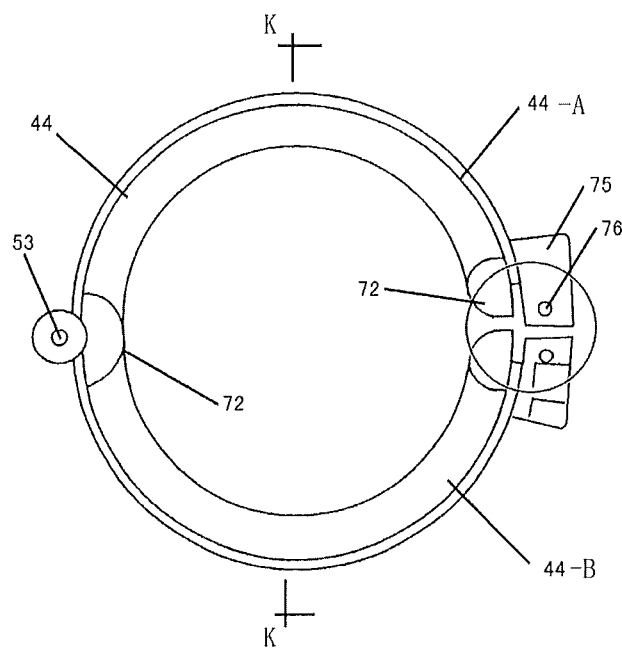
FIG. 29 illustrates the configuration of the tubular outer ring of an anastomat for circumcision according still another example in the present invention.
Figure 30:
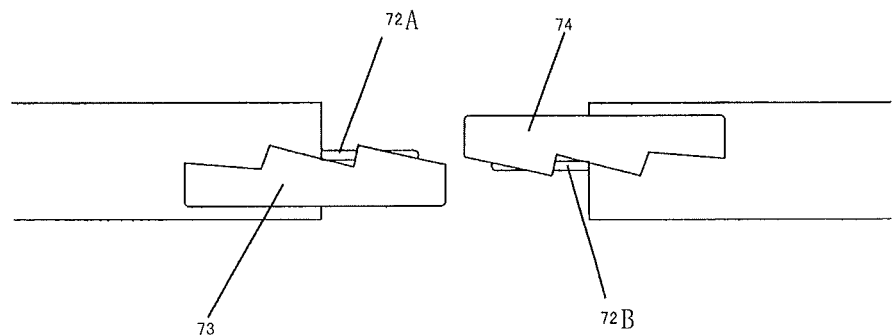
FIG. 30 illustrates the enlarged sectional details of part A in FIG. 29.

Additionally, as shown in FIG. 27 and FIG. 28, in another embodiment, the outer ring 44 comprises a semicircle part 44-A provided with an upper knife edge 72A junction thereon, and a semicircle part 44-B provided with a lower knife edge 72B junction which is corresponding to the upper knife edge 72A junction. Such configuration allows the outer ring 44 to be well connected. Each of said knife edge junction is provided with a round corner 72 at its fringe which allows the foreskin prevented from being clamped during the operation, thus to ensure the operation successfully and avoid pains. If the foreskin was clamped, a granulation would be formed, which may extend the time for healing and increase the suffering. Similarly, a same or similar round corner may be arranged on the junction of the left and right semicircle parts in the inner ring, so that the foreskin can be prevented from being clamped.

When used, the present invention will not cause pains or obvious scar. Instead, it provides an accurate position where the rings will fall from the affected part, as well as a faster healing. The treatment based on the present invention is suitable for the children, youth and aged. Moreover, the type of the anastomat may be selected depending on the actual size of the glans.

Furthermore, when used, the anastomat for circumcision in the present invention will not influence normal working and studying, and it can be easily operated without special training, which allows the treatment based on the present invention even can be implemented in a mini clinic. The present invention is further beneficial by its low price. The total cost for the whole period of treatment including the surgery, antiphlogosis and the same is only 160-200 yuan, which is publicly acceptable.

The present invention provides an anastomat for circumcision. Since its configuration of only arranging an upper casing pipe and a lower casing pipe in the upper part and lower part of the inner cutting ring I and outer cutting ring III respectively which are connected through a connecting plate or connecting rod, the anastomat for circumcision has a reduced weight. Furthermore, the upper casing pipe of the inner cutting ring I has an upper end face formed into patterns, which significantly relieves the suffering, when compared with known annular knife edge. Moreover, the connecting plate of the inner cutting ring I is additionally provided with a anti-erection plate V for preventing the penis from erection, which effectively avoids the suffering due to wound produced by penile erection. Besides, the graduated ruler arranged on the external side of the connecting rod of the outer cutting ring III may facilitate adjusting the crimping force produced between the outer cutting ring III and connecting ring IV depending on the thickness of the foreskin, as well as facilitate adjusting the cut deepness of the foreskin when a elevating cutting knife II is arranged between the outer cutting ring III and the connecting ring IV. In addition, since either the upper casing pipe or the lower casing pipe of the inner cutting ring I may be designed into a splicing ring, the inner diameter of the inner cutting ring I may be adjusted according to the requirement of patients. Due to its moveable configuration, the elevating cutting knife may be lifted up and withdrawn back as desired, which provides a flexible operation. Finally, the present anastomat for circumcision is a disposable product which prevents the disease spreading. Therefore, the present invention provides advantages such as small and exquisite, light weight, convenient to use, as well as low cost, and possesses the industrial applicability.

While preferred embodiments of the invention have been particularly shown and described, it should be understood that several changes and modifies may be made therein without departing from the technical principles of the invention for those skilled in the art, which should be also embraced in the protection range of the present invention.

The invention claimed is:

1. An anastomat for circumcision, comprising:
   an outer ring for cutting and clamping; and
   an inner ring for casing a foreskin, an external surface of said inner ring being provided with a recess, an inner side of said outer ring being provided with a knife edge, said knife edge being a double-layered knife edge or a single-layered knife edge provided with a plurality of projecting spots, said projecting spots being disposed inwardly and perpendicular to said knife edge, and said knife edge being fitted with said recess to extrude or cut off the foreskin, said outer ring being formed into two semicircular split rings or an integrated flexible split ring, each having an opening, said opening forming two ends which are provided with an upper knife edge junction and a corresponding lower knife edge junction, respectively, said upper knife edge junction and said lower knife edge junction being of an overlapping structure.

2. An anastomat for circumcision, comprising:
   an outer ring for cutting and clamping; and
   an inner ring for casing a foreskin, an external surface of said inner ring being provided with a recess, an inner side of said outer ring being provided with a knife edge; said knife edge being fitted with said recess to extrude or cut off the foreskin; saw teeth being arranged at said knife edge.

3. The anastomat for circumcision of claim 2, wherein said inner ring consists of a whole ring, two semicircles, or more than two arc segments.

4. The anastomat for circumcision of claim 3, wherein said recess is provided with an elastic washer at its surface.

5. The anastomat for circumcision of claim 4, wherein there is at least one channel arranged on a side wall of said outer ring for injecting medicine solution which are communicated with an empty cavity between said outer ring and said inner ring.

6. The anastomat for circumcision of claim 2, wherein said opening provides two ends which are connected with each other through a connecting snap.

7. The anastomat for circumcision of claim 6, wherein said opening has one end provided with a graduated ruler or a digital ruler for displaying dates indicating a tightness degree of the snap-fit, and another end provided with an alarm for reminding an overly tight snap-fitted situation or information of wound healing.

8. The anastomat for circumcision of claim 7, wherein an end of said opening, where an upper knife edge junction is arranged, is provided with a first ladder snap-fitted block, while another end of said opening, where a lower knife edge junction is arranged, is provided with a second ladder snap-fitted block, and said first ladder snap-fitted block and said second ladder snap-fitted block are fitted with each other; each of said first ladder snap-fitted block and said second ladder snap-fitted block is formed as single-layered or double-layered; said first ladder snap-fitted block is arranged below the upper knife edge junction, and said second ladder snap-fitted block is arranged above the lower knife edge junction.

9. The anastomat for circumcision of claim 8, wherein there are frosted patterns arranged on said outer ring and said inner ring.

10. The anastomat for circumcision of claim 7, wherein either end of said opening is provided with an unlocking stem and an unlocking hole.

11. The anastomat for circumcision of claim 10, wherein an upper knife edge junction and a lower knife edge junction are provided with a hook-like protuberance or a slotted hole respectively, wherein the hook-like protuberance or slotted hole arranged on one junction is fitted with the slotted hole or hook-like protuberance arranged on the other junction; each of said hook-like protuberances is comprising a connecting plate and an inverted-V-type clamping piece, wherein said connecting plate has one end connecting to a middle part of the clamping piece.

12. The anastomat for circumcision of claim 10, wherein an upper knife edge junction and a lower knife edge junction are provided with concave slotted holes respectively; said concave slotted holes receives a bow tie-like block.

13. The anastomat for circumcision of claim 10, wherein an upper knife edge junction and a lower knife edge junction are provided with bar-type denticles or bar-type sprocket holes respectively, wherein the bar-type denticle or bar-type sprocket hole arranged at one junction is fitted with the bar-type sprocket hole or bar-type denticle arranged on the other junction.

14. The anastomat for circumcision of claim 2, wherein said opening of which has two ends which are provided with an upper knife edge junction and a corresponding lower knife edge junction respectively; a fringe of each of said upper knife edge junction and said lower knife edge junction is provided with a round corner.

15. The anastomat for circumcision of claim 14, wherein said upper knife edge junction and said lower knife edge junction are locked and fixed through a screw stem.

16. The anastomat for circumcision of claim 14, wherein said upper knife edge junction and said lower knife edge junction are provided with L-shaped parts respectively which are fitted with each other; each of said L-shaped parts is provided with a connecting rod at its top end and a connecting hole on a platform at its bottom end; wherein the connecting rod of one L-shaped part is fitted with the connecting hole of the other L-shaped part; each of said L-shaped parts has a vertical end whose internal side is provided with a dentoid protuberance or dentoid groove, wherein the dentoid protuberance or dentoid groove of one L-shaped part is fitted with the dentoid groove or dentoid protuberance of the other L-shaped part.

17. The anastomat for circumcision of claim 2, wherein there are several cutting blades vertical to a double-layered knife edge sandwiched therebetween; a single-layered knife edge or double-layered knife edge is coated with anti-infection coating.

* * * * *